(12) United States Patent
Lee

(10) Patent No.: US 6,371,954 B1
(45) Date of Patent: Apr. 16, 2002

(54) PORTABLE LASER NEEDLE

(76) Inventor: Jung Koo Lee, 19-6 Songpa-dong, Songpa-ku, Seoul (KR)

( * ) Notice: Subject to any disclaimer, the term of this patent is extended or adjusted under 35 U.S.C. 154(b) by 0 days.

(21) Appl. No.: 09/455,636

(22) Filed: Dec. 7, 1999

(30) Foreign Application Priority Data

Oct. 22, 1999 (KR) .......................................... 99-45999

(51) Int. Cl.⁷ .............................................. A61B 18/18
(52) U.S. Cl. ....................................... 606/13; 606/189
(58) Field of Search .............................. 606/2, 15, 13, 606/3, 14, 17, 19, 189; 607/89, 3

(56) References Cited

U.S. PATENT DOCUMENTS

| | | | | | |
|---|---|---|---|---|---|
| 5,250,068 | A | * | 10/1993 | Ideguchi et al. | 606/189 |
| 5,609,562 | A | * | 3/1997 | Kaali | 66/114 |
| 5,988,832 | A | * | 11/1999 | Chen | 362/259 |
| 6,013,096 | A | * | 1/2000 | Tucek | 606/89 |
| 6,022,126 | A | * | 2/2000 | Sekine et al. | 362/259 |
| 6,027,224 | A | * | 2/2000 | Schnell | 362/119 |
| 6,119,944 | A | * | 9/2000 | Mulla et al. | 235/472.03 |
| 6,152,918 | A | * | 11/2000 | Padilla et al. | 606/15 |
| 6,158,431 | A | * | 12/2000 | Poole | 128/203.12 |

* cited by examiner

Primary Examiner—Michael Peffley

(57) ABSTRACT

A laser needle device for acupuncture which is portable, relatively inexpensive and easy to use. The device includes a retractable ceramic needle and a self-contained laser source, which is powered by a self-contained battery. The ceramic needle engages the end of a hollow ray passage member that is contained in the conical distal end of an elongate case. Finger-generated depression of a button at the opposite end of the case generates a mechanical force, transmitted by intermediate elements, to ultimately urge spring-actuated downward movement of the ray passage member so that the needle tip emerges from an opening in the conical distal end of the case. The self-contained battery delivers power to a laser generating chip housed in the case when the downward movement of the intermediate elements complete an electrical circuit with two contacting terminals, simultaneous with the emergence of the needle tip, whereupon the chip generates a laser ray which passes through a lens, through the ray passage member and through the aperture of the needle.

2 Claims, 4 Drawing Sheets

PORTABLE LASER NEEDLE

BACKGROUND OF THE INVENTION

1. Field of the Invention

This invention relates to a laser needle for treating ailments of the human body, and more particularly to a portable laser needle for acupuncture having a self-contained laser source, which is powered by a self-contained battery.

2. Description of the Prior Art

In Chinese medical science, needle-based acupuncture is one of the therapies commonly used for curing various diseases.

However, only practitioners who have undergone special training for acupuncture may administer this therapy. Also, a metal needle is used in acupuncture, resulting in increased pain during treatment and scarring that remains after treatment. Metal needles also may transmit infectious diseases from one patient to another with improper sterilization techniques. For these reasons, most potential acupuncture patients are inclined to avoid this treatment.

The development of laser needle usage in acupuncture has eliminated these problematic aspects, as the use of a laser ray in treatment does not cause extensive pain, does not leave a scar, and does not pose the risk of infection. In addition, the use of laser needles has allowed those without special training in traditional techniques to practice acupuncture therapy without difficulty.

Unfortunately, laser needle usage in acupuncture can be problematic as well.

The standard laser needle is often separate from the elevating instrument required for use on patients, complicating the administration of the acupuncture therapy. Standard laser needles are considerably large, making their portability impossible, and thereby forcing patients to seek treatment at facilities having laser needles for acupuncture, often at their inconvenience. Another problem is the enormous expense incurred by the use of laser needles, involving high costs of installation, operation and maintenance. These shortcomings all account for the limited use of standard laser needles in acupuncture.

SUMMARY OF THE INVENTION

The portable laser needle device of the present invention addresses and overcomes the problems associated with metal acupuncture needles and standard laser needles.

The portable laser needle of the present invention comprises an elongate case having distal and proximal ends. A push button at the proximal end engages a driving member via a spring, and the driving member engages a slidable interior housing structure. The housing structure contains a battery and a laser assembly comprising a laser ray generating chip, a laser ray generating element and a condensing lens. A ray passage member extends from the distal end of the housing structure to the conical bottom part of the case, passing through an elongate laser projection opening. The distal end of the ray passage member engages a ceramic needle though which a laser ray passes. Another spring encircles the ray passage member.

A set of two contacting terminals form an electrical circuit incorporating the battery, the laser assembly and a resistor. The end of one of the contact terminals hangs proximate to the inside surface of the case bottom when the ceramic needle is not deployed.

In use, depression of the push button urges the spring-actuated downward movement of both the battery and the housing structure, causing two events to occur simultaneously. First, the ray passage member is pushed in a downward direction, moving the ceramic needle so that it emerges from the distal tip. At the same time, the end of the hanging contact terminal is lowered to engage the inside surface of the case bottom, completing the electrical circuit that transfers power from the battery to the laser ray generating chip, causing it to generate a laser ray that passes through the condensing lens, the ray passage member and the ceramic needle to ultimately reach the patient's body and achieve the intended therapeutic effect.

After use, further depression of the push button initiates spring-actuated upward movement of the driving member and the housing structure, causing both the retraction of the ceramic needle and the hanging contact terminal to disengage the inside surface of the case bottom. This results in a short-circuiting of the flow of electric power from the battery to the laser ray generating chip that stops radiation of the laser ray at the same time ceramic needle retracts.

The preferred embodiment of the invention is of a size similar to a ball-point pen or the like, facilitating ease of transport and use. A clip secures the device in the pocket of a user for improved accessability and convenience.

The portable laser needle of this invention provides for a simplified structure and operation, enabling a user who is not a trained acupuncture specialist to practice acupuncture techniques as well.

Furthermore, the portability and relative inexpensiveness of the device of the present invention increase the availability of this therapy, more so than with the current usage of stationary standard laser needles for acupuncture.

Accordingly, the principle object of this invention is to provide a laser needle for acupuncture usage that is portable, and of a convenient size.

It is another object of this invention to provide alternate means for administrating acupuncture therapy that does not have the pain-related, scarring-related or infection risk-related shortcomings of traditional metal acupuncture needles.

It is a further object of this invention to provide a simple effective laser needle for use in acupuncture therapy by persons not specifically trained in acupuncture techniques.

It is yet another object of this invention to provide a laser needle for acupuncture that is not separate from the elevating instrument, to simplify administration of acupuncture therapy.

It is still another object of this invention to provide a relatively inexpensive yet effective laser needle for use in acupuncture therapy.

BRIEF DESCRIPTIONS OF THE DRAWINGS

DESCRIPTION OF THE PREFERRED EMBODIMENT

Figure 1:
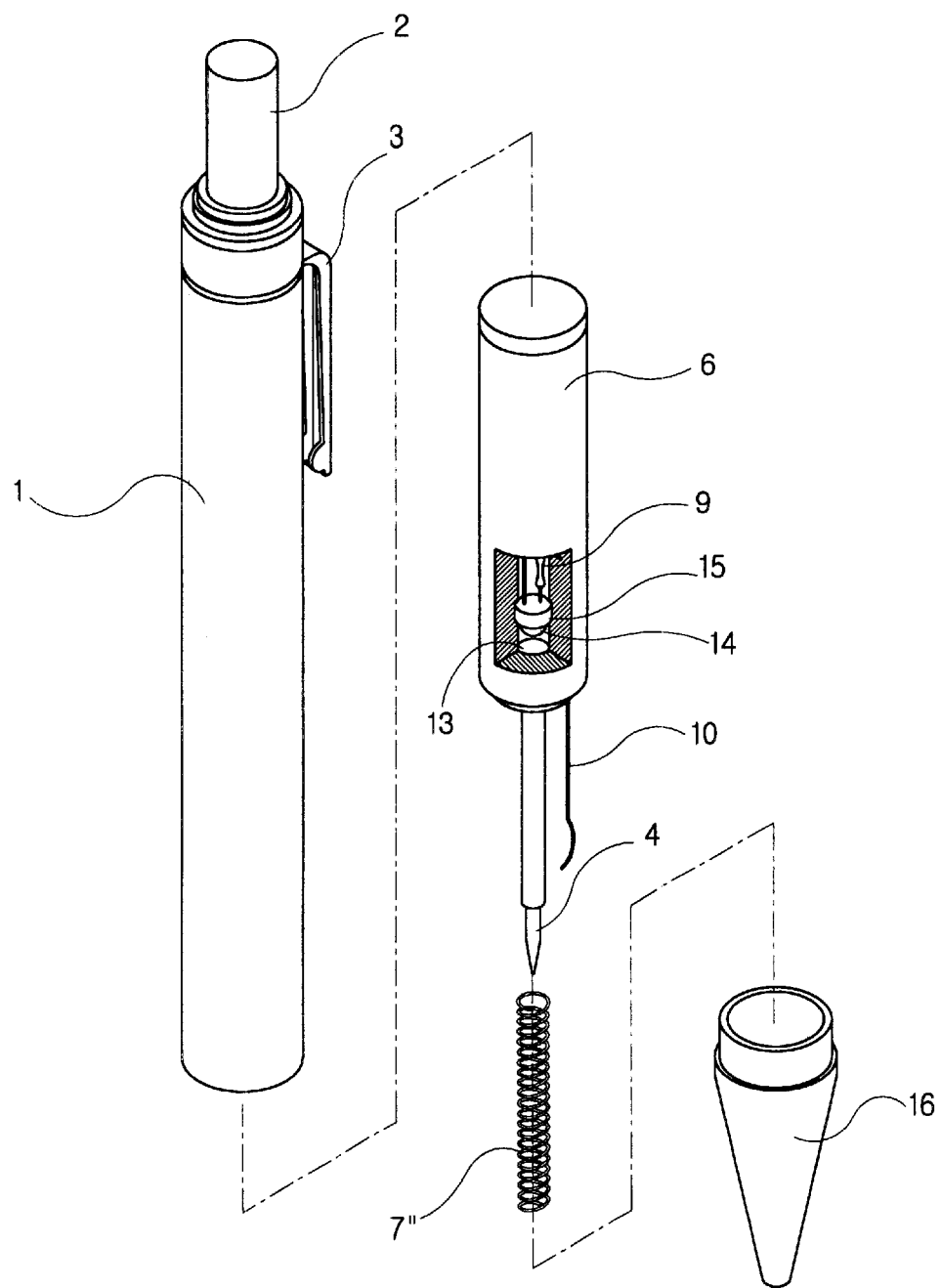
FIG. 1 is an exploded perspective view of the PORTABLE LASER NEEDLE of the present invention.
Figure 2A:
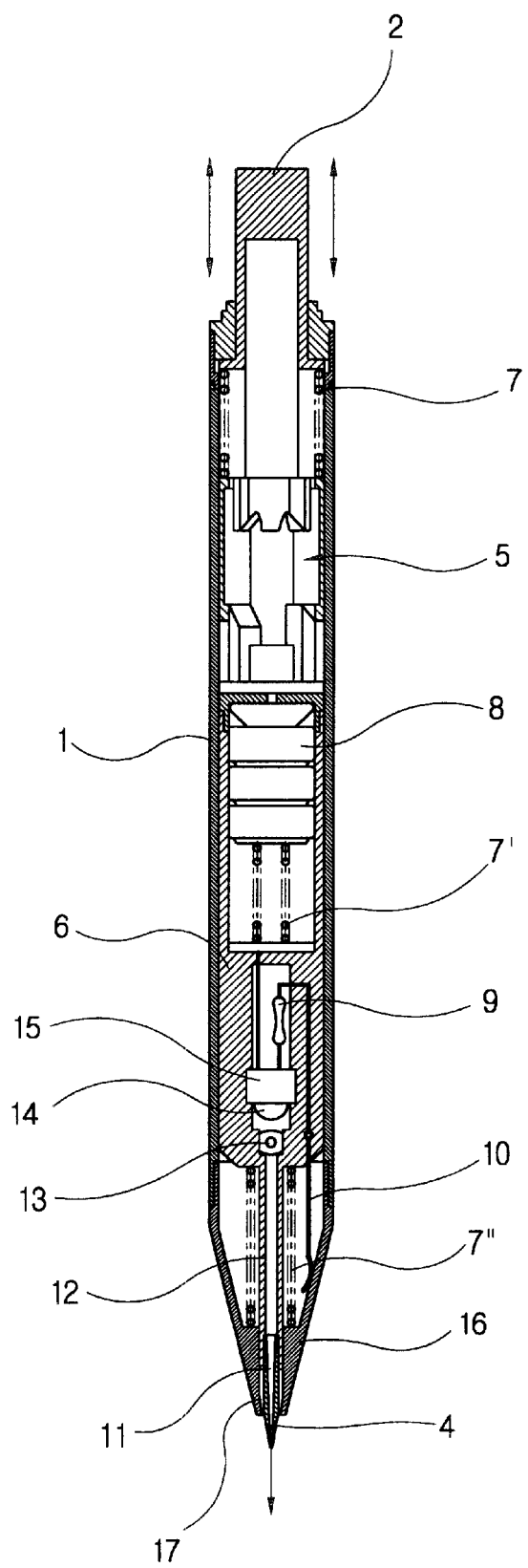
FIG. 2a is a sectional view thereof, with the ceramic needle deployed.
Figure 2B:
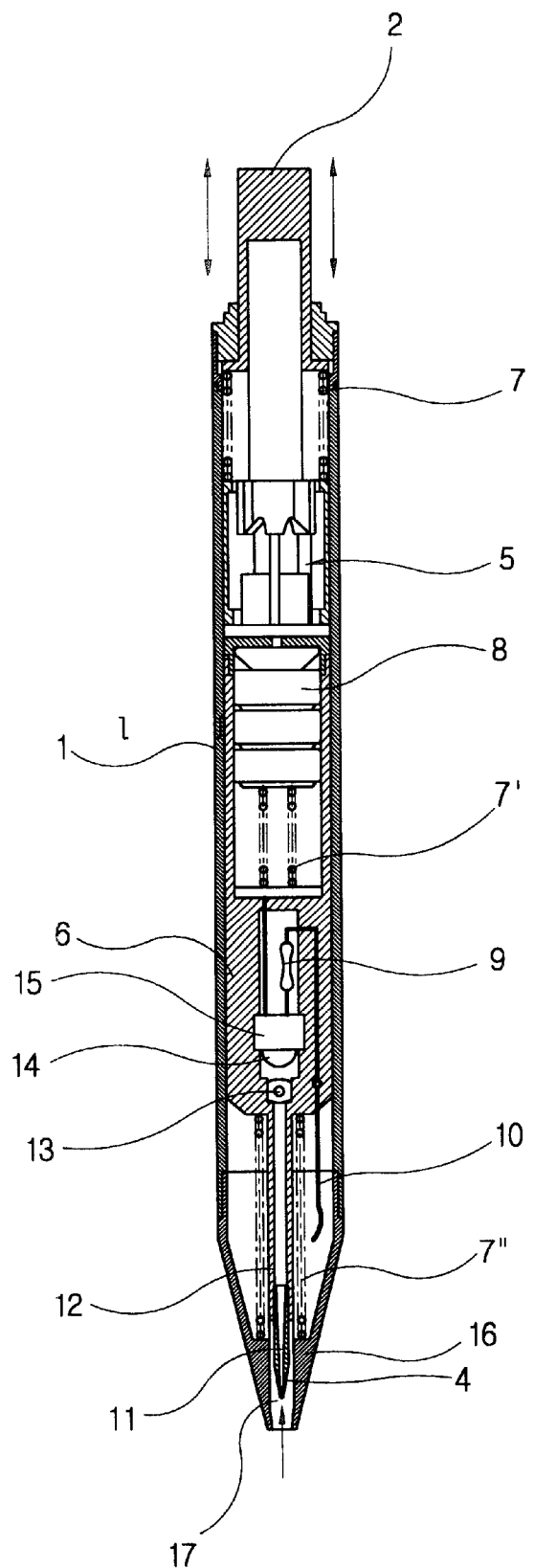
FIG. 2b is a sectional view thereof, with the ceramic needle retracted.

Referring now to FIGS. 1, 2a and 2b, the portable laser needle of the present invention comprises an elongate case 1 having distal and proximal ends. A push button 2 is disposed at the proximal end of case 1 and engages one end of a first spring 7. The opposing end of spring 7 engages a driving member 5, which in turn engages a slidable interior housing structure 6 within case 1. Housing structure 6 contains a battery 8, which engages one end of a second spring 7, in a battery compartment. The other end of spring 7' engages the bottom of the battery compartment.

Housing structure 6 also contains the laser assembly, which comprises a laser ray generating chip 15, a laser ray generating element 14, a condensing lens 13 and the proximal end of a ray passage member 12. Ray passage member 12 extends from the distal end of housing structure 6 to the conical bottom part 16 of case 1. Ray passage member 12 passes through the elongate laser projection opening 17 defined by case bottom 16. The distal end of ray passage member 12 engages a ceramic needle 4, which defines an aperture 11, though which a laser ray passes at the distal tip of bottom 16. A third spring 7" encircles the length of ray passage member 12. One end of spring 7" engages the distal part of housing structure 6, and the opposing end engages the proximal part of case bottom 16.

A set of two contacting terminals 10 interconnect battery 8 and the laser assembly as follows: The opposing ends of the first contact terminal 10 engage battery 8, through the bottom of the battery compartment and spring 7', and laser generating chip 15, respectively. One end of the second contact terminal 10 also engages laser generating chip 15, passes through a resistor 9 and through housing structure 6 to extend from the distal portion thereof, whereby the other end of contact terminal 10 hangs freely in case 1, proximate to the inside surface of case bottom 16 and spring 7", as shown in FIG. 2b.

Referring now to FIG. 1, which shows an exploded view of the components of the present invention, pocket clip 3 extends from case 1 at a point distal to push button 2.

The operation of the laser needle according to this invention as above will be described below.

When the laser needle of this invention is used, as shown in FIG. 2a, the laser needle is placed at the site of human body for laser needle acupuncture and then the button 2 of the rotary elevating instrument 5 projected at the top is pushed to shift the lower part of the rotary elevating instrument 5 downward to maintain the pushed state thereof.

The user performing an acupuncture technique first places the laser needle at the site designated for treatment on the patient's body. Initially, ceramic needle 4 is contained within laser projection opening 17 when the device is not in use, as shown in FIG. 2b. The user depresses push button 2, as shown in FIG. 2a, urging the spring-actuated downward movement of driving member 5. The movement of driving member 5 in turn urges the spring-actuated downward movement of both battery 8 and housing structure 6.

Figure 3:
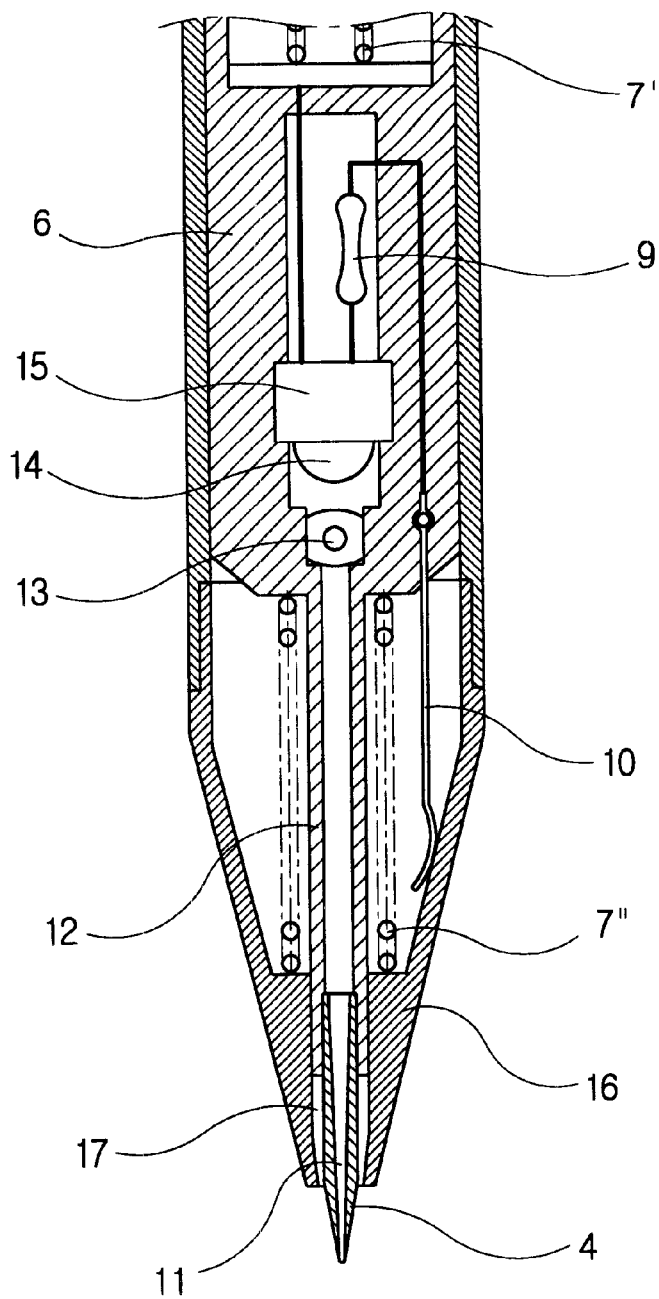
FIG. 3 is a detailed sectional view thereof, showing the distal portion thereof.

The downward movement of housing structure 6 causes two events to occur simultaneously. First, ray passage member 12 is pushed in a downward direction through projection opening 17, moving ceramic needle 4 so that the tip of the needle emerges therefrom, exterior to the distal end of case bottom 16. At the same time, the end of hanging contact terminal 10 is lowered to a point where it engages the inside surface of case bottom 16, as shown in FIG. 2a and in more detail in FIG. 3. This initiates the completion of a electrical circuit, whereby power from battery 8 is delivered to laser ray generating chip 15, causing it to generate a laser ray from element 14.

The laser ray then passes through condensing lens 13, which changes it to a linear ray. The linear laser ray then passes through ray passage member 12 and through aperture 11 of ceramic needle 4 to ultimately reach the patient's body and achieve the intended therapeutic effect.

Following the application of the laser needle for the acupuncture procedure, the user may again depress push button 2 to initiate the spring-actuated upward movement of driving member 5 and housing structure 6. This in turn causes the retraction of ray passage member 12 and ceramic needle 4 into projection opening 17 of case bottom 16, as shown in FIG. 2b.

Depression of push button 2 and the resultant upward movement of housing structure 6 also displaces hanging contact terminal 10, disengaging it from the inside surface of case bottom 16 and short-circuiting the passage of electric power from battery 8 to laser ray generating chip 18, ultimately stopping radiation of the laser ray at the same time ceramic needle 4 retracts.

The preferred embodiment of the invention is of a size similar to a ball-point pen or the like, facilitating ease of transport and use. Clip 3 secures the device in the pocket of a user for improved accessability and convenience.

The portable laser needle of this invention provides for a simplified structure and operation, enabling a user who is not a trained acupuncture specialist to practice acupuncture techniques as well.

Furthermore, the portability and relative inexpensiveness of the device of the present invention increase the availability of this therapy, more so than with the current usage of stationary standard laser needles for acupuncture.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense. Therefore, the spirit and scope of this invention are limited solely by the appended claims.

What is claimed is:

1. A portable hand-holdable laser device for emitting a laser light, said hand-holdable device having a distal housing, said housing having a distal tip, a self-contained power source within said housing, a condensing lens contained within the housing to direct the laser light into and through a hollow ceramic acupuncture needle, said acupuncture needle being slidable and contained inside said housing distal tip, a substantially simultaneously electrical power connection being connected at a same time as said ceramic needle is slidingly moved into a projecting space past said distal tip of said needle housing, said movable needle being held within the distal tip by a spring contained within said housing when the power source is not activated, and said activation being activated by an operator's finger pressing a movable plunger located at the proximal end of said device.

2. The portable hand-holdable laser device according to claim 1, said device being a size of a ball point pen.

* * * * *